United States Patent
Masui et al.

(10) Patent No.: US 10,092,163 B2
(45) Date of Patent: Oct. 9, 2018

(54) ENDOSCOPE APPARATUS, ENDOSCOPE, INITIALIZATION METHOD, AND INITIALIZATION PROGRAM

(71) Applicant: SONY OLYMPUS MEDICAL SOLUTIONS INC., Tokyo (JP)

(72) Inventors: Ichiro Masui, Chiba (JP); Takahiro Yamamoto, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 109 days.

(21) Appl. No.: 15/122,505

(22) PCT Filed: Mar. 25, 2015

(86) PCT No.: PCT/JP2015/059164
§ 371 (c)(1),
(2) Date: Aug. 30, 2016

(87) PCT Pub. No.: WO2015/147070
PCT Pub. Date: Oct. 1, 2015

(65) Prior Publication Data
US 2017/0086647 A1  Mar. 30, 2017

(30) Foreign Application Priority Data

Mar. 28, 2014 (JP) ................................ 2014-068537
Jan. 23, 2015 (JP) ................................ 2015-011762

(51) Int. Cl.
*A61B 1/04* (2006.01)
*A61B 1/00* (2006.01)
(Continued)

(52) U.S. Cl.
CPC ...... *A61B 1/00006* (2013.01); *A61B 1/00009* (2013.01); *A61B 1/00025* (2013.01);
(Continued)

(58) Field of Classification Search
CPC ... A61B 1/05; A61B 1/00057; A61B 1/00096; A61B 1/00045; A61B 1/042;
(Continued)

(56) References Cited

U.S. PATENT DOCUMENTS

| 5,840,017 A * | 11/1998 | Furusawa | ......... A61B 1/00186 600/160 |
| 6,508,760 B2 * | 1/2003 | Yamanaka | ......... A61B 1/00096 348/240.99 |

(Continued)

FOREIGN PATENT DOCUMENTS

| JP | 2010-4979 A | 1/2010 |
| JP | 2010-284274 A | 12/2010 |

(Continued)

OTHER PUBLICATIONS

International Search Report dated Jun. 30, 2015 in PCT/JP2015/059164 filed Mar. 25, 2015.

*Primary Examiner* — Dramos I Kalapodas
(74) *Attorney, Agent, or Firm* — Oblon, McClelland, Maier & Neustadt, L.L.P.

(57) ABSTRACT

An endoscope apparatus includes: a camera head configured to examine an interior of a subject and output a result of the examination; and a control apparatus electrically connected to the camera head and configured for the examination result to be inputted thereto from the camera head and to control operation of the camera head. The camera head includes a plurality of devices, and a CPU configured to perform initialization of at least one of the plurality of devices. The endoscope apparatus makes it possible to shorten start-up time of the entire endoscope apparatus.

6 Claims, 2 Drawing Sheets

(51) Int. Cl.
    *H04N 5/232* (2006.01)
    *H04N 5/225* (2006.01)
(52) U.S. Cl.
    CPC ...... *A61B 1/00045* (2013.01); *A61B 1/00057* (2013.01); *A61B 1/00188* (2013.01); *A61B 1/04* (2013.01); *H04N 5/23212* (2013.01); *H04N 5/23241* (2013.01); *H04N 5/23254* (2013.01); *H04N 5/23296* (2013.01); *H04N 5/2256* (2013.01); *H04N 2005/2255* (2013.01)
(58) Field of Classification Search
    CPC ....... A61B 1/00193; A61B 1/041; A61B 1/04; A61B 1/06; A61B 1/045; H04N 7/183; H04N 19/597; H04N 13/044; H04N 13/0239; H04N 13/0434; H04N 13/0296; H04N 13/0059; H04N 13/0025; H04N 13/0459; H04N 13/0217; H04N 13/0285; H04N 13/0037; H04N 13/0048; H04N 13/0055; H04N 13/0257; H04N 5/772; H04N 5/2628; H04N 5/44513; H04N 5/23296; H04N 5/23293; H04N 2005/2255; H04N 5/14; H04N 5/262; H04N 7/18; Y10S 600/921
    See application file for complete search history.

(56) References Cited

U.S. PATENT DOCUMENTS

| | | | |
|---|---|---|---|
| 8,531,479 B2* | 9/2013 | Doi | A61B 1/00045 345/581 |
| 9,629,523 B2* | 4/2017 | Tesar | A61B 17/02 |
| 2002/0158973 A1* | 10/2002 | Gomi | H04N 5/23293 348/240.2 |
| 2008/0055429 A1* | 3/2008 | Yoshida | H04N 5/2628 348/240.99 |
| 2011/0004059 A1* | 1/2011 | Arneson | A61B 1/00041 600/109 |
| 2012/0062715 A1 | 3/2012 | Endo et al. | |
| 2012/0209064 A1* | 8/2012 | Numata | A61B 1/00057 600/109 |
| 2015/0238073 A1* | 8/2015 | Charles | A61B 17/02 600/102 |

FOREIGN PATENT DOCUMENTS

| | | |
|---|---|---|
| JP | 2011-112861 A | 6/2011 |
| JP | 2011-156262 A | 8/2011 |
| JP | 2011-177263 A | 9/2011 |
| JP | 2013-9908 A | 1/2013 |

* cited by examiner

ENDOSCOPE APPARATUS, ENDOSCOPE, INITIALIZATION METHOD, AND INITIALIZATION PROGRAM

TECHNICAL FIELD

The present invention relates to an endoscope apparatus, an endoscope, an initialization method, and an initialization program.

BACKGROUND ART

Thus far, in the medical field and the industrial field, an endoscope apparatus that uses an imaging element to image the interior of an object to be observed such as a person or a machine structure to observe the interior of the object to be observed has been known (e.g. see Patent Literature 1).

The endoscope apparatus described in Patent Literature 1 includes an endoscope that includes a camera head including an imaging element and a transmission cable electrically connected to the camera head and a control apparatus that controls the operation of the camera head via the transmission cable.

In an endoscope apparatus like the above, an initialization operation like below is performed at the start-up of the endoscope apparatus.

FIG. 4 is a timing chart for describing the initialization operation of a conventional endoscope apparatus. Specifically, in FIG. 4, the initialization operation of the control apparatus is illustrated in the top, the initialization operation of the camera head is illustrated in the middle, and the state of the endoscope apparatus is illustrated in the bottom.

First, when the power switch in the control apparatus is set to ON (timing T1' shown in FIG. 4), a power supply voltage is supplied from the power supply unit in the control apparatus to each device in the control apparatus, and the control apparatus starts the initialization of the control apparatus itself.

After the start of the initialization of the control apparatus, the control apparatus supplies the camera head with electric power necessary for the driving of the camera head via the transmission cable (timing T2' shown in FIG. 4).

When the initialization of the control apparatus is completed (timing T3' shown in FIG. 4), the control apparatus starts the initialization of the camera head. Then, the control apparatus enters and remains in the standby state until the initialization of the camera head is completed.

When the initialization of the camera head is completed (timing T4' shown in FIG. 4), the control apparatus and the camera head enter the steady state. That is, the endoscope apparatus enters the steady state (a state in which the interior of the object to be observed can be observed) at this timing T4'.

CITATION LIST

Patent Literature

Patent Literature 1: JP 2011-177263A

SUMMARY OF INVENTION

Technical Problem

However, in the initialization operation of the conventional endoscope apparatus, since it is the control apparatus that executes the initialization of the camera head, the initialization of the camera head is executed after the initialization of the control apparatus is completed. That is, there is a problem that the time from when the power switch is set to ON to when the endoscope apparatus enters the steady state (the start-up time) is long.

The present invention has been made in view of the above, and an object of the present invention is to provide an endoscope apparatus, an endoscope, an initialization method, and an initialization program that make it possible to shorten the start-up time of the entire endoscope apparatus.

Solution to Problem

To solve the above problem and achieve the object, an endoscope apparatus according to the present invention includes: an endoscope configured to examine an interior of a subject and output a result of the examination; and a control apparatus electrically connected to the endoscope and configured for the examination result to be inputted thereto and to control operation of the endoscope. The endoscope includes a plurality of devices, and an initialization processing unit configured to perform initialization of at least one of the plurality of devices.

In the invention, in the endoscope apparatus according to the present invention, while the control apparatus performs initialization of the control apparatus itself, the initialization processing unit may perform initialization of at least one of the plurality of devices in parallel with the initialization of the control apparatus.

In the invention, in the endoscope apparatus according to the present invention, the initialization processing unit may start initialization of at least one of the plurality of devices with a start of electric power supply from the control apparatus to the endoscope as a trigger.

In the invention, in the endoscope apparatus according to the present invention, the plurality of devices may include an imaging unit configured to image the interior of the subject, and the initialization processing unit may perform initialization of the imaging unit.

In the invention, in the endoscope apparatus according to the present invention, the plurality of devices may include a lens unit configured to collect light in a prescribed visual field area and allow at least one of a focus position and a zoom position to be altered, and a driving unit configured to alter at least one of the focus position and the zoom position, and the initialization processing unit may set at least one of the focus position and the zoom position in the lens unit to an initial position, as the initialization of at least one of the plurality of devices.

In the invention, in the endoscope apparatus according to the present invention, the endoscope may include an imaging unit configured to image the interior of the subject as one of the plurality of devices and output an imaging signal generated by imaging by the imaging unit as the examination result. The control apparatus may include a first image processing unit configured to perform image processing on the imaging signal to generate a first imaging signal for display and output the first imaging signal for display, and a second image processing unit configured to perform image processing on the imaging signal to generate a second imaging signal for display and output the second imaging signal for display. The endoscope apparatus may include a display apparatus configured for the first imaging signal for display or the second imaging signal for display to be inputted thereto and to display a captured image based on the first imaging signal for display or the second imaging signal for display inputted. The control apparatus may output, when the imaging signal is inputted from the endoscope after initialization of the control apparatus is completed, the first imaging signal for display generated in the first image processing unit to the display apparatus, and output, when the imaging signal is inputted from the endoscope while initialization of the control apparatus is being performed, the second imaging signal for display generated in the second image processing unit to the display apparatus.

An endoscope according to the present invention is an endoscope electrically connected to a control apparatus and configured to output an examination result of an interior of a subject to the control apparatus, the endoscope including: a plurality of devices; and an initialization processing unit configured to perform initialization of at least one of the plurality of devices.

In the invention, in the endoscope according to the present invention, an imaging unit configured to image the interior of the subject as one of the plurality of devices may be included. The endoscope may output an imaging signal generated by imaging by the imaging unit as the examination result.

An initialization method according to the present invention is an initialization method to be executed by an endoscope electrically connected to a control apparatus and configured to output an examination result of an interior of a subject to the control apparatus, the endoscope including a plurality of devices, and an initialization processing unit configured to perform initialization of at least one of the plurality of devices, the initialization method including: while the control apparatus performs initialization of the control apparatus itself, performing initialization of at least one of the plurality of devices in the initialization processing unit in parallel with the initialization of the control apparatus.

An initialization program according to the present invention is configured to cause an endoscope to execute the above initialization method.

Advantageous Effects of Invention

In the endoscope apparatus according to the present invention, the endoscope includes an initialization processing unit that performs the initialization of at least one of the plurality of devices constituting the endoscope.

That is, the endoscope executes the initialization of the endoscope by itself. Thus, the time when the initialization of the endoscope is executed is not after the initialization of the control apparatus is completed, but the initialization of the endoscope can be executed in parallel with the initialization of the control apparatus. Therefore, the effect of allowing the start-up time of the entire endoscope apparatus to be shortened is exhibited.

The endoscope according to the present invention is an endoscope used for the endoscope apparatus described above, and therefore exhibits a similar effect to the endoscope apparatus described above.

The initialization method according to the present invention is an initialization method that the endoscope described above executes, and therefore exhibits a similar effect to the endoscope described above.

The initialization program according to the present invention is a program to be executed by the endoscope described above, and therefore exhibits a similar effect to the endoscope described above.

DESCRIPTION OF EMBODIMENT(S)

Figure 1:
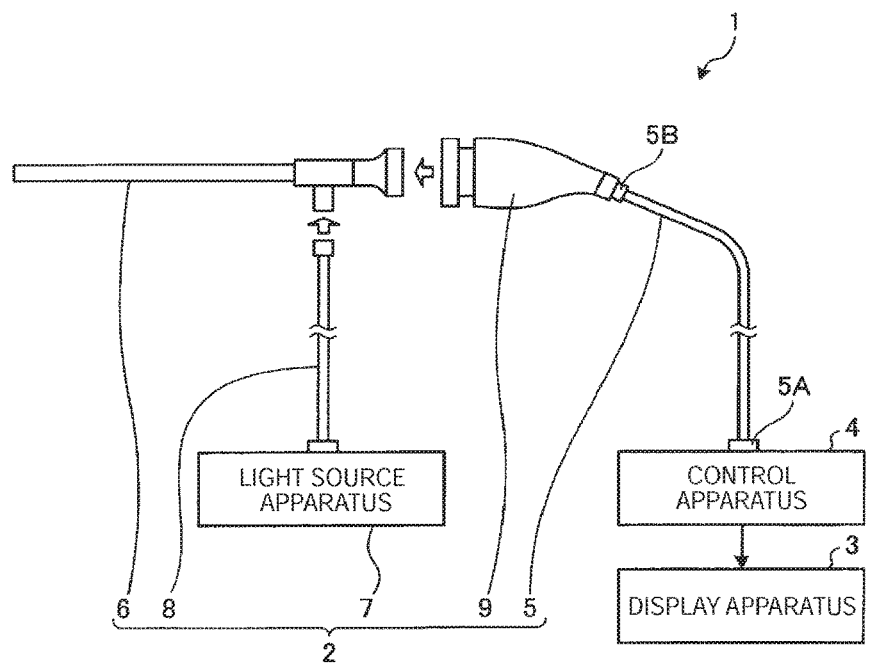
FIG. 1 is a diagram showing a rough configuration of an endoscope apparatus according to an embodiment of the present invention.

Hereinbelow, embodiments of the present invention (hereinafter, embodiments) are described with reference to the drawings. The present invention, however, is not limited by the embodiments described below. In the description of the drawings, identical portions are marked with the same reference numerals.

<Rough Configuration of the Endoscope Apparatus>

FIG. 1 is a diagram showing a rough configuration of an endoscope apparatus 1 according to an embodiment of the present invention.

The endoscope apparatus 1 is used in the medical field, and is an apparatus that observes the interior of an object to be observed such as a person (the interior of a living body). The endoscope apparatus 1 includes, as shown in FIG. 1, an endoscope 2, a display apparatus 3, and a control apparatus 4.

Although in the embodiment an endoscope apparatus using a rigid scope (an insertion unit 6 (FIG. 1)) in the endoscope 2 is described as the endoscope apparatus 1, the endoscope apparatus 1 is not limited to this, and may be an endoscope apparatus using a flexible scope (illustration omitted) in the endoscope 2. Further, although in the embodiment an endoscope apparatus using a camera head 9 (FIG. 1) in the endoscope 2 is described as the endoscope apparatus 1, the endoscope apparatus 1 is not limited to this, and may be an endoscope apparatus in which the endoscope 2 is formed of a probe for ultrasonography (an ultrasonic endoscope).

The endoscope 2 examines the interior of a living body (the interior of a subject) and outputs the examination result. The endoscope 2 includes, as shown in FIG. 1, a transmission cable 5, an insertion unit 6, a light source apparatus 7, a light guide 8, and a camera head 9.

The insertion unit 6 is rigid and has a long, thin shape, and is inserted into the interior of the living body. In the insertion unit 6, an optical system that is configured using one or a plurality of lenses and optically collects a subject image is provided.

One end of the light guide 8 is connected to the light source apparatus 7, and the light source apparatus 7 supplies the one end of the light guide 8 with light for lighting up the interior of the living body.

One end of the light guide 8 is connected to the light source apparatus 7 in an attachable and detachable manner, and the other end of the light guide 8 is connected to the insertion unit 6 in an attachable and detachable manner. The light guide 8 transmits the light supplied from the light source apparatus 7 from the one end to the other end, and supplies the light to the insertion unit 6. The light supplied to the insertion unit 6 is emitted from the tip of the insertion unit 6, and is applied to the interior of the living body. The light applied to the interior of the living body (a subject image) is optically collected by the optical system in the insertion unit 6.

The camera head 9 is connected to the root end of the insertion unit 6 in an attachable and detachable manner. Under the control of the control apparatus 4, the camera head 9 captures a subject image optically collected by the insertion unit 6, and outputs an imaging signal based on the imaging (corresponding to an examination result according to the present invention).

In the embodiment, the camera head 9 photoelectrically converts the imaging signal to an optical signal, and outputs the imaging signal as the optical signal.

Here, the camera head 9 is not limited to a configuration that outputs the imaging signal as an optical signal, and may be configured to output the imaging signal as an electrical signal.

A detailed configuration of the camera head 9 is described later.

The transmission cable 5 includes a first connector unit 5A (FIG. 1) at one end, and is connected to the control apparatus 4 via the first connector unit 5A in an attachable and detachable manner. Further, the transmission cable 5 includes a second connector unit 5B (FIG. 1) at the other end, and is connected to the camera head 9 via the second connector unit 5B in an attachable and detachable manner. The transmission cable 5 is specifically a cable in which a plurality of electrical interconnections (illustration omitted) and an optical fiber (illustration omitted) are provided inside a covering that is the outermost layer.

The plurality of electrical interconnections are electrical interconnections for transmitting a control signal, a synchronization signal, a clock, and electric power, respectively, outputted from the control apparatus 4 to the camera head 9.

The optical fiber is an optical fiber for transmitting an imaging signal (an optical signal) outputted from the camera head 9 to the control apparatus 4. Here, in the case where the imaging signal is outputted from the camera head 9 as an electrical signal, the optical fiber may be replaced with an electrical interconnection.

The display apparatus 3 displays an image under the control of the control apparatus 4.

The control apparatus 4 is configured to include a central processing unit (CPU) etc., and comprehensively controls the operation of the camera head 9 and the display apparatus 3.

A detailed configuration of the control apparatus 4 is described later.

<Configuration of the Camera Head and the Control Apparatus>

Next, the configuration of the camera head 9 and the control apparatus 4 is described.

Figure 2:
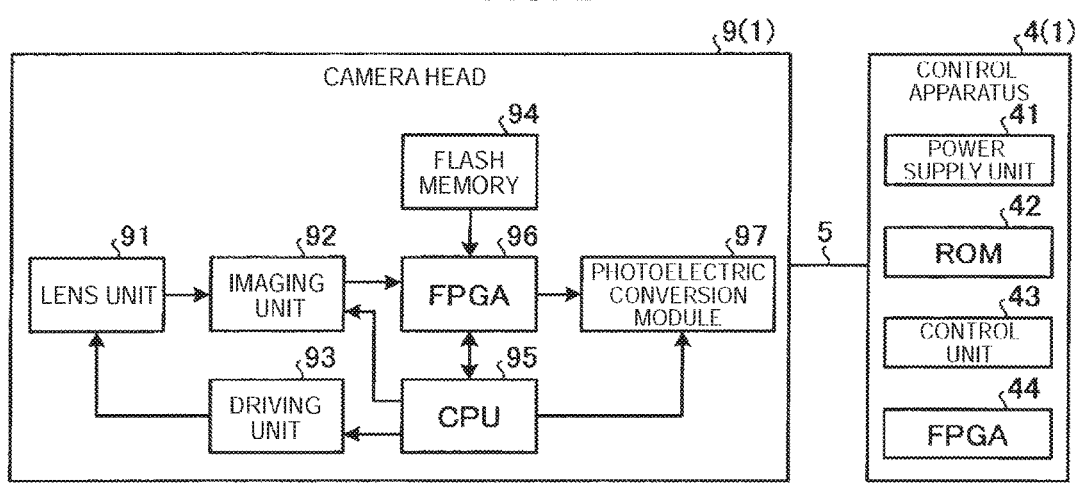
FIG. 2 is a block diagram showing the configuration of the camera head and the control apparatus shown in FIG. 1.

FIG. 2 is a block diagram showing the configuration of the camera head 9 and the control apparatus 4.

In FIG. 2, the illustration of the connector (the second connector unit 5B) that allows the camera head 9 and the transmission cable 5 to be attachable to and detachable from each other and the connector (the first connector unit 5A) that allows the transmission cable 5 and the control apparatus 4 to be attachable to and detachable from each other is omitted. Further, in FIG. 2, the plurality of electrical interconnections and the optical fiber constituting the transmission cable 5 are illustrated as one cable for convenience of description.

The configuration of the control apparatus 4 and the configuration of the camera head 9 will now be described in this order.

<Configuration of the Control Apparatus>

In the following, the principal part of the present invention is mainly described as the configuration of the control apparatus 4.

The control apparatus 4 includes, as shown in FIG. 2, a power supply unit 41, a read-only memory (ROM) 42, a control unit 43, and a field programmable gate array (FPGA) 44.

The power supply unit 41 generates a power supply voltage for driving the control apparatus 4 and the camera head 9, and supplies the power supply voltage to the parts 42 to 44 of the control apparatus 4 and supplies the power supply voltage to the camera head 9 via the transmission cable 5.

The ROM 42 records various programs that the control unit 43 executes, configuration data for configuring the FPGA 44, which is a programmable integrated circuit (the rewriting of the logic circuit), etc.

The control unit 43 is configured using a CPU, a graphics processing unit (GPU), etc., and controls the operation of the control apparatus 4 and the camera head 9.

Specifically, the control unit 43 (a GPU etc.) photoelectrically converts an imaging signal (an optical signal) inputted from the camera head 9 via the transmission cable 5 to an electrical signal, performs various image processings such as noise reduction, color correction, color enhancement, and contour enhancement on the photoelectrically converted imaging signal and generates a first imaging signal for display, and outputs the first imaging signal for display to the display apparatus 3. Upon the input of the first imaging signal for display, the display apparatus 3 displays a captured image based on the first imaging signal for display.

That is, the control unit 43 has a function as a first image processing unit according to the present invention.

Furthermore, the control unit 43 reads the configuration data recorded in the ROM 42 to configure the FPGA 44, which is a programmable integrated circuit.

Moreover, the control unit 43 outputs a control signal, a synchronization signal (e.g. a synchronization signal that indicates the imaging timing of the camera head 9, etc.), and a clock (a clock for serial communication) to the camera head 9 via the transmission cable 5.

The FPGA 44 is a logic circuit configured by the control unit 43.

Specifically, the FPGA 44 performs various image processings (image processings simpler than the image processings performed by the control unit 43 described above (with a lower processing load)) on an imaging signal inputted from the camera head 9 via the transmission cable 5 and generates a second imaging signal for display, and outputs the second imaging signal for display to the display apparatus 3. Upon the input of the second imaging signal for display, the display apparatus 3 displays a captured image based on the second imaging signal for display.

That is, the FPGA 44 has a function as a second image processing unit according to the present invention.

<Configuration of the Camera Head>

In the following, the principal part of the present invention is mainly described as the configuration of the camera head 9.

The camera head 9 includes, as shown in FIG. 2, a lens unit 91, an imaging unit 92, a driving unit 93, a flash memory 94, a CPU 95, an FPGA 96, and a photoelectric conversion module 97.

The members 91 to 97 correspond to devices according to the present invention.

The lens unit 91 is configured using one or a plurality of lenses, and forms a subject image optically collected by the insertion unit 6 on the imaging surface of an imaging element (illustration omitted) included in the imaging unit 92. The one or plurality of lenses are configured movably along the optical axis. In the lens unit 91, an optical zoom mechanism (illustration omitted) that moves the one or plurality of lenses to change the angle of view and a focus mechanism (illustration omitted) that moves the one or plurality of lenses to change the focus are provided.

The imaging unit 92 images the interior of the living body under the control of the CPU 95. The imaging unit 92 is configured using a sensor chip in which an imaging element (illustration omitted) that receives a subject image formed by the lens unit 91 and converts the subject image to an electrical signal, such as a charge-coupled device (CCD) or a complementary metal oxide semiconductor (CMOS), a signal processing unit (illustration omitted) that performs signal processing (A/D conversion etc.) on the electrical signal (an analog signal) from the imaging element and outputs an imaging signal, etc. are integrally formed.

The driving unit 93 puts the optical zoom mechanism and the focus mechanism into operation to change the angle of view and the focus of the lens unit 91, under the control of the CPU 95.

The flash memory 94 records configuration data for configuring the FPGA 96, which is a programmable integrated circuit (the rewriting of the logic circuit), etc.

The CPU 95 controls the operation of the entire camera head 9 in accordance with a control signal inputted from the control apparatus 4 via the transmission cable 5, an instruction signal outputted from an operating part provided to be exposed on the outer surface of the camera head 9, such as a switch, by the user's operation on the operating part, etc., in conformity with various programs (including an initialization program) recorded in an internal memory (illustration omitted). Furthermore, the CPU 95 outputs the information on the current state of the camera head 9 to the control apparatus 4 via the transmission cable 5.

The CPU 95 according to the embodiment has a function as an initialization processing unit that performs the initialization of the members 91 to 97, which function is specifically described later. The "initialization" is a processing that differs between the members 91 to 97. Thus, the CPU 95 performs initialization on the members 91 to 97 sequentially or in parallel in accordance with a prescribed procedure (an initialization program).

The FPGA 96 is a programmable integrated circuit, and reads the configuration data recorded in the flash memory 94 and executes configuration (the rewriting of the logic circuit) independently.

Then, the FPGA 96 generates a clock for imaging that is for driving the imaging unit 92 and a clock for driving that is for driving the driving unit 93 on the basis of a reference clock generated by an oscillator (illustration omitted) provided in the camera head 9, and outputs the clocks to the imaging unit 92 and the driving unit 93, respectively. Furthermore, the FPGA 96 generates timing signals of various processings in the imaging unit 92, the driving unit 93, and the CPU 95 on the basis of a synchronization signal inputted from the control apparatus 4 via the transmission cable 5, and outputs the timing signals to the imaging unit 92, the driving unit 93, and the CPU 95, respectively.

Thereby, the imaging unit 92 operates with the clock for imaging inputted from the FPGA 96, and under the control of the CPU 95, performs imaging and the output of an imaging signal at a timing based on the timing signal inputted from the FPGA 96. Furthermore, the driving unit 93 operates with the clock for driving inputted from the FPGA 96, and under the control of the CPU 95, puts the optical zoom mechanism and the focus mechanism into operation to adjust the angle of view and the focus of the lens unit 91.

Furthermore, the FPGA 96 converts an imaging signal outputted from the imaging unit 92 to an imaging signal in accordance with a prescribed transmission manner. Then, the FPGA 96 outputs the converted imaging signal to the photoelectric conversion module 97 on the basis of a clock for data transfer generated by an oscillator (illustration omitted) provided in the camera head 9.

The photoelectric conversion module 97 photoelectrically converts the imaging signal (an electrical signal) outputted from the FPGA 96 to an optical signal, and transfers the converted imaging signal (an optical signal) to the control apparatus 4 via the transmission cable 5 (the optical fiber).

<Operation of the Endoscope Apparatus>

Next, the operation of the endoscope apparatus 1 described above is described.

In the following, the initialization operation of the endoscope apparatus 1 (an initialization method according to the present invention) is mainly described as the operation of the endoscope apparatus 1.

Figure 3:
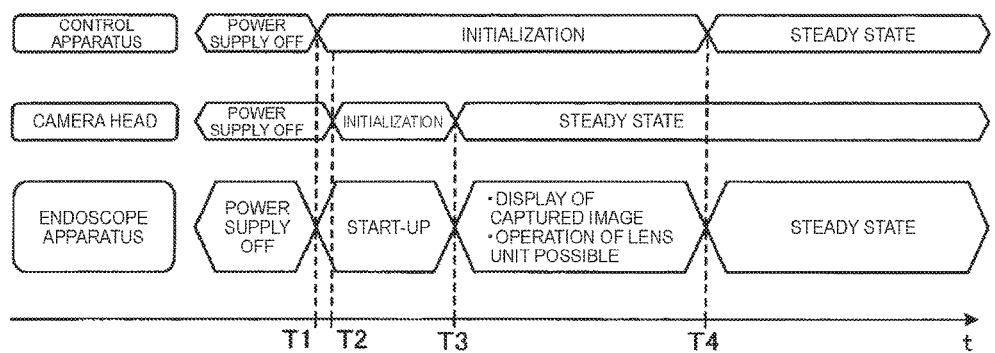
FIG. 3 is a timing chart for describing the initialization operation of the endoscope apparatus shown in FIG. 1 or FIG. 2.
Figure 4:
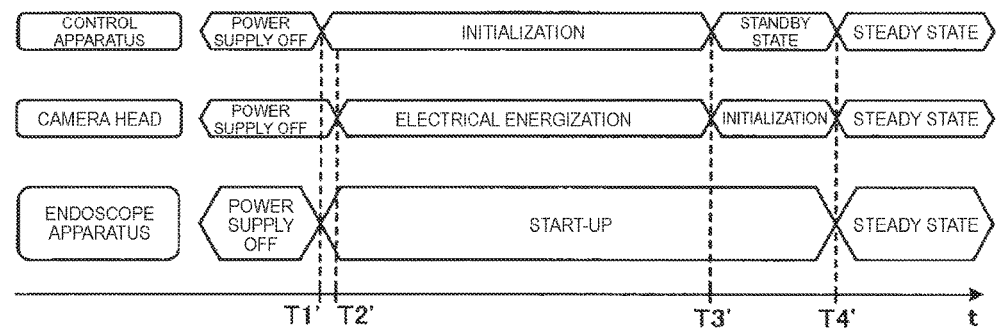
FIG. 4 is a timing chart for describing the initialization operation of a conventional endoscope apparatus.

FIG. 3 is a timing chart for describing the initialization operation of the endoscope apparatus 1. Specifically, in FIG. 3, the initialization operation of the control apparatus 4 is illustrated in the top, the initialization operation of the camera head 9 is illustrated in the middle, and the state of the endoscope apparatus 1 is illustrated in the bottom.

First, when the power switch in the control apparatus 4 is set to ON (timing T1 shown in FIG. 3), the power supply unit 41 supplies the generated power supply voltage to the parts 42 to 44 of the control apparatus 4. Then, the control unit 43 starts the initialization of the control apparatus 4 (the initialization of the GPU included in the control apparatus 4, the configuration of the FPGA 44, etc.). After the start timing of the initialization of the control apparatus 4, the power supply unit 41 supplies the generated power supply voltage to the camera head 9 via the transmission cable 5 (timing T2 shown in FIG. 3). Further, the control apparatus 4 outputs a synchronization signal and a clock to the camera head 9 via the transmission cable 5.

Next, with the start of the supply of the power supply voltage from the control apparatus 4 (timing T2 shown in FIG. 3) as a trigger, the camera head 9 (the CPU 95) starts the initialization of the camera head 9. That is, the CPU 95 performs the initialization of the camera head 9 in parallel with the initialization of the control apparatus 4.

For example, the following processing is executed as the initialization of the camera head 9.

The CPU 95 performs the initialization of a register etc. provided inside. Further, the CPU 95 transmits a prescribed reset signal (a pulse signal) to a device reset terminal (illustration omitted) provided as a chip terminal of the imaging unit 92 to perform the initialization of the imaging unit 92. Further, while recognizing a signal outputted from a position detection unit (illustration omitted) that detects the focus position and the zoom position of the lens unit 91, such as a Hall element, the CPU 95 controls the operation of the driving unit 93 to set the focus position and the zoom position to the initial positions. The FPGA 96 reads the configuration data recorded in the flash memory 94, and executes configuration independently.

When the initialization of the camera head 9 described above is completed (timing T3 shown in FIG. 3), the camera head 9 enters the steady state.

In this steady state, the camera head 9 is in a state in which the angle of view and the focus of the lens unit 91 can be adjusted when the operating part provided to be exposed on the outer surface of the camera head 9, such as a switch, is operated. That is, the driving unit 93 operates with the clock for driving inputted from the FPGA 96, and when the operating part is operated, adjusts the angle of view and the focus of the lens unit 91 under the control of the CPU 95.

Furthermore, in this steady state, the camera head 9 is in a state of sequentially outputting imaging signals generated in the imaging unit 92 to the control apparatus 4 via the transmission cable 5. That is, on the basis of a clock for data transfer generated by an oscillator (illustration omitted) provided in the camera head 9, the FPGA 96 sequentially outputs imaging signals generated in the imaging unit 92 (imaging signals converted in accordance with a prescribed transmission manner) to the photoelectric conversion module 97. Then, the photoelectric conversion module 97 photoelectrically converts the imaging signal (an electrical signal) outputted from the FPGA 96 to an optical signal, and transfers the optical signal to the control apparatus 4 via the transmission cable 5 (the optical fiber).

Here, the control apparatus 4 completes the configuration of the FPGA 44 in the period from when the initialization of the control apparatus 4 itself is started to when the initialization of the camera head 9 is completed (the period from timing T1 to T3 shown in FIG. 3). Then, in the period in which the camera head 9 is in the steady state and yet the initialization of the control apparatus 4 is not completed (the period from timing T3 to T4 shown in FIG. 3), when an imaging signal is inputted from the camera head 9 via the transmission cable 5, the control apparatus 4 outputs a second imaging signal for display generated in the FPGA 44 to the display apparatus 3. Then, the display apparatus 3 displays a captured image based on the inputted second imaging signal for display (an image that has undergone image processing in a simple manner in the FPGA 44).

Then, when the initialization of the control apparatus 4 is completed (timing T4 shown in FIG. 3), the control apparatus 4 enters the steady state, and the entire endoscope apparatus 1 enters the steady state.

In this steady state, when an imaging signal is inputted from the camera head 9 via the transmission cable 5, the control apparatus 4 outputs a first imaging signal for display generated in the control unit 43 (a GPU) to the display apparatus 3. Then, the display apparatus 3 displays a captured image based on the inputted first imaging signal for display (an image that has undergone image processing in the control unit 43 (a GPU)).

In the endoscope apparatus 1 according to the embodiment described above, the camera head 9 includes the CPU 95, and executes the initialization of the camera head 9 by itself.

Thus, the time when the initialization of the camera head 9 is executed is not after the initialization of the control apparatus 4 is completed, but the initialization of the camera head 9 can be executed in parallel with the initialization of the control apparatus 4. Therefore, the effect of allowing the start-up time of the entire endoscope apparatus 1 to be shortened is exhibited.

Furthermore, the camera head 9 according to the embodiment starts the initialization of itself with the start of the electric power supply from the control apparatus 4 to the camera head 9 via the transmission cable 5 as a trigger.

Thus, the initialization of the camera head 9 can be started quickly, and the effect described above can be obtained more satisfactorily.

The camera head 9 according to the embodiment performs, as the initialization of the camera head 9 itself, the initialization of the imaging unit 92 and the initialization of the lens unit 91 and the driving unit 93. In the period in which the initialization of the control apparatus 4 is not completed, when an imaging signal is inputted from the camera head 9 via the transmission cable 5, the control apparatus 4 causes a captured image that has undergone image processing in a simple manner in the FPGA 44, not in the control unit 43 (a GPU), to be displayed on the display apparatus 3.

Thus, even when the camera head 9 is in the steady state and yet the initialization of the control apparatus 4 is not completed, a captured image can be displayed on the display apparatus 3, and furthermore the angle of view and the focus of the lens unit 91 can be adjusted by operating the operating part provided to be exposed on the outer surface of the camera head 9.

Other Embodiments

Hereinabove, an embodiment of the present invention is described, but the present invention is not limited to the embodiment described above.

Although in the embodiment described above the CPU 95 performs the initialization of the entire camera head 9, the configuration is not limited to this, and also a configuration in which the initialization of some devices of the parts 91 to 97 constituting the camera head 9 is performed by the CPU 95 and the initialization of the other devices is executed by the control apparatus 4 is possible. Also in this configuration, the object of the present invention can be achieved when the initialization of the some devices is performed in parallel with the initialization of the control apparatus 4.

Although in the embodiment described above the CPU 95 (an initialization processing unit according to the present invention) is provided in the camera head 9, the configuration is not limited to this, and also a configuration in which the CPU 95 is provided in, for example, the first connector unit 5A or the second connector unit 5B may be employed as long as the CPU 95 is provided in the endoscope 2.

Although in the embodiment described above the CPU 95 starts the initialization of the camera head 9 with the start of the electric power supply from the control apparatus 4 to the camera head 9 via the transmission cable 5 as a trigger, the configuration is not limited to this. The initialization of the camera head 9 may be performed at other timings as long as the initialization of the camera head 9 and the initialization of the control apparatus 4 can be performed in parallel.

Although in the embodiment described above the lens unit 91 is configured to allow both of the focus position and the zoom position to be altered, the configuration is not limited to this, and also a configuration in which either one of the focus position and the zoom position can be altered may be employed.

In the embodiment described above, the endoscope apparatus 1 may be configured as an endoscope apparatus that is used not only in the medical field but also in the industrial field and observes the interior of an object to be observed such as a machine structure.

REFERENCE SIGNS LIST 1 endoscope apparatus
2 endoscope
3 display apparatus
4 control apparatus 5 transmission cable
6 insertion unit
7 light source apparatus
8 light guide
9 camera head
41 power supply unit
42 ROM
43 control unit
44 FPGA
91 lens unit
92 imaging unit
93 driving unit
94 flash memory
95 CPU
96 FPGA
97 photoelectric conversion module
T1 to T4, T1' to T4' timing

The invention claimed is:

1. An endoscope apparatus comprising:
an endoscope configured to examine an interior of a subject and output a result of the examination;
a control apparatus detachably connected to the endoscope and configured to receive an examination result and to control operation of the endoscope, wherein
the endoscope includes an imaging sensor and an endoscope circuit,
the control apparatus includes a control apparatus circuit,
the endoscope circuit and the control apparatus circuit perform a parallel initialization, and
the parallel initialization includes a first initialization by the endoscope circuit to initialize the image sensor and a second initialization by the control apparatus circuit to initialize the control apparatus.

2. The endoscope apparatus according to claim 1, wherein the endoscope circuit starts initialization of the image sensor with a start of electric power supply from the control apparatus to the endoscope as a trigger.

3. The endoscope apparatus according to claim 1, wherein the endoscope includes:
a lens configured to collect light in a prescribed visual field area and allow at least one of a focus position and a zoom position to be altered; and
a driver configured to alter at least one of the focus position and the zoom position, and
the endoscope circuit sets at least one of the focus position and the zoom position in the lens to an initial position, as the first initialization.

4. The endoscope apparatus according to claim 1, wherein
the image sensor is configured to image the interior of the subject and output an imaging signal as the examination result,
the control apparatus includes:
a first image processing circuit configured to perform image processing on the imaging signal to generate a first imaging signal for display and output the first imaging signal for display; and
a second image processing circuit configured to perform image processing on the imaging signal to generate a second imaging signal for display and output the second imaging signal for display,
the endoscope apparatus includes a display configured to receive the first imaging signal for display or the second imaging signal for display and to display a captured image based on the received first imaging signal for display or the received second imaging signal for display, and
the control apparatus is configured to:
output, when the imaging signal is inputted from the endoscope after initialization of the control apparatus is completed, the first imaging signal for display generated in the first image processing circuit to the display; and
output, when the imaging signal is inputted from the endoscope while initialization of the control apparatus is being performed, the second imaging signal for display generated in the second image processing circuit to the display.

5. An initialization method to be executed by an endoscope detachably connected to a control apparatus and configured to output an examination result of an interior of a subject to the control apparatus, the method comprising:
examining, using the endoscope, an interior of a subject and output a result of the examination;
receiving, using the control apparatus, the examination result and controlling, using the control apparatus, operation of the endoscope, wherein
the endoscope includes an imaging sensor and an endoscope circuit,
the control apparatus includes a control apparatus circuit,
the method further comprises performing, using the endoscope circuit and the control apparatus circuit, a parallel initialization, and
the parallel initialization includes a first initialization by the endoscope circuit to initialize the image sensor and a second initialization by the control apparatus circuit to initialize the control apparatus.

6. A non-transitory computer readable medium including executable instructions, which when executed by a computer cause the computer to execute an initialization method to be executed by an endoscope detachably connected to a control apparatus and configured to output an examination result of an interior of a subject to the control apparatus, the method comprising:
examining, using the endoscope, an interior of a subject and output a result of the examination;
receiving, using the control apparatus, the examination result and controlling, using the control apparatus, operation of the endoscope, wherein
the endoscope includes an imaging sensor and an endoscope circuit,
the control apparatus includes a control apparatus circuit,
the method further comprises performing, using the endoscope circuit and the control apparatus circuit, a parallel initialization, and
the parallel initialization includes a first initialization by the endoscope circuit to initialize the image sensor and a second initialization by the control apparatus circuit to initialize the control apparatus.

* * * * *